(12) United States Patent
Gale et al.

(10) Patent No.: US 7,329,366 B1
(45) Date of Patent: Feb. 12, 2008

(54) METHOD OF POLISHING IMPLANTABLE MEDICAL DEVICES TO LOWER THROMBOGENECITY AND INCREASE MECHANICAL STABILITY

(75) Inventors: David C. Gale, San Jose, CA (US); Syed F. A. Hossainy, Fremont, CA (US)

(73) Assignee: Advanced Cardiovascular Systems Inc., Santa Clara, CA (US)

( * ) Notice: Subject to any disclaimer, the term of this patent is extended or adjusted under 35 U.S.C. 154(b) by 237 days.

(21) Appl. No.: 10/871,404

(22) Filed: Jun. 18, 2004

Related U.S. Application Data (63) Continuation-in-part of application No. 10/603,889, filed on Jun. 25, 2003.

(51) Int. Cl.
*B44C 1/22* (2006.01)

(52) U.S. Cl. .............. 216/88; 216/37; 216/39; 216/11; 216/41; 216/91; 216/103; 427/2.24; 427/98.8; 427/485; 427/541; 623/1.15; 623/1.38; 623/901

(58) Field of Classification Search .......... 216/37, 216/88; 427/2.24, 98.8; 623/1.15, 1.38
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,329,383 A | 5/1982 | Joh |
| 4,346,028 A | 8/1982 | Griffith |
| 4,596,574 A | 6/1986 | Urist |
| 4,599,085 A | 7/1986 | Riess et al. |

(Continued)

FOREIGN PATENT DOCUMENTS

DE 44 07 079 9/1994

(Continued)

OTHER PUBLICATIONS

U.S. Appl. No. 10/317,435, filed Dec. 11, 2002, Hossainy et al.

(Continued)

*Primary Examiner*—Nadine Norton
*Assistant Examiner*—Maki Angadi
(74) *Attorney, Agent, or Firm*—Squire, Sanders & Dempsey (57) ABSTRACT

The present invention relates to a method of polishing an implantable medical device. The method may include positioning an implantable medical device on a support. At least a portion of a surface of the implantable medical device may include a polymer. A fluid may be contacted with at least a portion of the surface of the positioned implantable medical device. In an embodiment, the fluid may be capable of dissolving at least a portion of the polymer at or near the surface of the implantable medical device. The method may further include allowing the fluid to modify at least a portion of the surface of the positioned medical device. A majority of the contacted fluid may be removed from the surface of the implantable medical device. In certain embodiments, the modified portion of the surface may be substantially less thrombogenetic and substantially more mechanically stable than an unmodified surface.

21 Claims, 4 Drawing Sheets

U.S. PATENT DOCUMENTS

| | | |
|---|---|---|
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,882,168 A | 11/1989 | Casey et al. |
| 4,886,062 A | 12/1989 | Wiktor |
| 4,902,289 A | 2/1990 | Yannas |
| 4,941,870 A | 7/1990 | Okada et al. |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,165,919 A | 11/1992 | Sasaki et al. |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,272,012 A | 12/1993 | Opolski |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,292,516 A | 3/1994 | Viegas et al. |
| 5,298,260 A | 3/1994 | Viegas et al. |
| 5,300,295 A | 4/1994 | Viegas et al. |
| 5,306,286 A | 4/1994 | Stack et al. |
| 5,306,294 A | 4/1994 | Winston et al. |
| 5,306,501 A | 4/1994 | Viegas et al. |
| 5,328,471 A | 7/1994 | Slepian |
| 5,330,500 A | 7/1994 | Song |
| 5,330,768 A | 7/1994 | Park et al. |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,380,299 A | 1/1995 | Fearnot et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,417,981 A | 5/1995 | Endo et al. |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,569,463 A | 10/1996 | Helmus et al. |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,609,629 A | 3/1997 | Fearnot et al. |
| 5,618,299 A | 4/1997 | Khosravi et al. |
| 5,624,411 A | 4/1997 | Tuch |
| 5,628,730 A | 5/1997 | Shapland et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,658,995 A | 8/1997 | Kohn et al. |
| 5,667,767 A | 9/1997 | Greff et al. |
| 5,667,796 A | 9/1997 | Otten |
| 5,670,558 A | 9/1997 | Onishi et al. |
| 5,679,400 A | 10/1997 | Tuch |
| 5,693,085 A | 12/1997 | Buirge et al. |
| 5,700,286 A | 12/1997 | Tartaglia et al. |
| 5,702,754 A | 12/1997 | Zhong |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,735,897 A | 4/1998 | Buirge |
| 5,741,881 A | 4/1998 | Patnaik |
| 5,746,998 A | 5/1998 | Torchilin et al. |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,776,184 A | 7/1998 | Tuch |
| 5,780,807 A | 7/1998 | Saunders |
| 5,788,979 A | 8/1998 | Alt et al. |
| 5,800,392 A | 9/1998 | Racchini |
| 5,800,516 A | 9/1998 | Fine et al. |
| 5,811,447 A | 9/1998 | Kunz et al. |
| 5,820,917 A | 10/1998 | Tuch |

| | | | | | | |
|---|---|---|---|---|---|---|
| 5,824,048 | A | 10/1998 | Tuch | 6,099,562 | A | 8/2000 | Ding et al. |
| 5,824,049 | A | 10/1998 | Ragheb et al. | 6,103,230 | A | 8/2000 | Billiar et al. |
| 5,830,178 | A | 11/1998 | Jones et al. | 6,107,416 | A | 8/2000 | Patnaik et al. |
| 5,830,461 | A | 11/1998 | Billiar | 6,110,188 | A | 8/2000 | Narciso, Jr. |
| 5,830,879 | A | 11/1998 | Isner | 6,110,483 | A | 8/2000 | Whitbourne et al. |
| 5,833,651 | A | 11/1998 | Donovan et al. | 6,113,629 | A | 9/2000 | Ken |
| 5,834,582 | A | 11/1998 | Sinclair et al. | 6,117,979 | A | 9/2000 | Hendriks et al. |
| 5,836,962 | A | 11/1998 | Gianotti | 6,120,536 | A | 9/2000 | Ding et al. |
| 5,837,008 | A | 11/1998 | Berg et al. | 6,120,904 | A | 9/2000 | Hostettler et al. |
| 5,837,313 | A | 11/1998 | Ding et al. | 6,121,027 | A | 9/2000 | Clapper et al. |
| 5,837,835 | A | 11/1998 | Gryaznov et al. | 6,125,523 | A | 10/2000 | Brown et al. |
| 5,840,083 | A | 11/1998 | Braach-Maksvytis | 6,127,173 | A | 10/2000 | Eckstein et al. |
| 5,851,508 | A | 12/1998 | Greff et al. | 6,129,761 | A | 10/2000 | Hubbell |
| 5,853,408 | A | 12/1998 | Muni | 6,129,928 | A | 10/2000 | Sarangapani et al. |
| 5,854,207 | A | 12/1998 | Lee et al. | 6,150,630 | A | 11/2000 | Perry et al. |
| 5,855,612 | A | 1/1999 | Ohthuki et al. | 6,153,252 | A | 11/2000 | Hossainy et al. |
| 5,855,618 | A | 1/1999 | Patnaik et al. | 6,159,951 | A | 12/2000 | Karpeisky et al. |
| 5,858,746 | A | 1/1999 | Hubbell et al. | 6,160,084 | A | 12/2000 | Langer et al. |
| 5,865,814 | A | 2/1999 | Tuch | 6,165,212 | A | 12/2000 | Dereume et al. |
| 5,868,781 | A | 2/1999 | Killion | 6,166,130 | A | 12/2000 | Rhee et al. |
| 5,869,127 | A | 2/1999 | Zhong | 6,169,170 | B1 | 1/2001 | Gryaznov et al. |
| 5,873,904 | A | 2/1999 | Ragheb et al. | 6,171,609 | B1 | 1/2001 | Kunz |
| 5,874,101 | A | 2/1999 | Zhong et al. | 6,174,330 | B1 | 1/2001 | Stinson |
| 5,874,109 | A | 2/1999 | Ducheyne et al. | 6,177,523 | B1 | 1/2001 | Reich et al. |
| 5,874,165 | A | 2/1999 | Drumheller | 6,183,505 | B1 | 2/2001 | Mohn, Jr. et al. |
| 5,876,433 | A | 3/1999 | Lunn | 6,187,045 | B1 | 2/2001 | Fehring et al. |
| 5,876,743 | A | 3/1999 | Ibsen et al. | 6,203,551 | B1 | 3/2001 | Wu |
| 5,877,224 | A | 3/1999 | Brocchini et al. | 6,210,715 | B1 | 4/2001 | Starling et al. |
| 5,877,263 | A | 3/1999 | Patnaik et al. | 6,214,901 | B1 | 4/2001 | Chudzik et al. |
| 5,879,713 | A | 3/1999 | Roth et al. | 6,224,626 | B1 | 5/2001 | Steinke |
| 5,888,533 | A | 3/1999 | Dunn | 6,228,845 | B1 | 5/2001 | Donovan et al. |
| 5,891,192 | A | 4/1999 | Murayama et al. | 6,231,600 | B1 | 5/2001 | Zhong |
| 5,897,955 | A | 4/1999 | Drumheller | 6,240,616 | B1 | 6/2001 | Yan |
| 5,906,759 | A | 5/1999 | Richter | 6,245,076 | B1 | 6/2001 | Yan |
| 5,914,182 | A | 6/1999 | Drumheller | 6,245,103 | B1 | 6/2001 | Stinson |
| 5,916,870 | A | 6/1999 | Lee et al. | 6,245,753 | B1 | 6/2001 | Byun et al. |
| 5,922,005 | A | 7/1999 | Richter et al. | 6,248,344 | B1 | 6/2001 | Ylanen et al. |
| 5,925,720 | A | 7/1999 | Kataoka et al. | 6,251,135 | B1 | 6/2001 | Stinson et al. |
| 5,942,209 | A | 8/1999 | Leavitt et al. | 6,251,136 | B1 | 6/2001 | Guruwaiya et al. |
| 5,948,428 | A | 9/1999 | Lee et al. | 6,251,142 | B1 | 6/2001 | Bernacca et al. |
| 5,954,744 | A | 9/1999 | Phan et al. | 6,254,632 | B1 | 7/2001 | Wu et al. |
| 5,955,509 | A | 9/1999 | Webber et al. | 6,258,121 | B1 | 7/2001 | Yang et al. |
| 5,957,975 | A | 9/1999 | Lafont et al. | 6,273,913 | B1 | 8/2001 | Wright et al. |
| 5,965,720 | A | 10/1999 | Gryaznov et al. | 6,281,262 | B1 | 8/2001 | Shikinami |
| 5,971,954 | A | 10/1999 | Conway et al. | 6,283,947 | B1 | 9/2001 | Mirzaee |
| 5,976,182 | A | 11/1999 | Cox | 6,283,949 | B1 | 9/2001 | Roorda |
| 5,980,564 | A | 11/1999 | Stinson | 6,284,305 | B1 | 9/2001 | Ding et al. |
| 5,980,928 | A | 11/1999 | Terry | 6,284,333 | B1 | 9/2001 | Wang et al. |
| 5,980,972 | A | 11/1999 | Ding | 6,287,332 | B1 | 9/2001 | Bolz et al. |
| 5,981,568 | A | 11/1999 | Kunz et al. | 6,287,628 | B1 | 9/2001 | Hossainy et al. |
| 5,986,169 | A | 11/1999 | Gjunter | 6,290,721 | B1 | 9/2001 | Heath |
| 5,997,468 | A | 12/1999 | Wolff et al. | 6,293,966 | B1 | 9/2001 | Frantzen |
| 5,997,517 | A | 12/1999 | Whitbourne | 6,299,604 | B1 | 10/2001 | Ragheb et al. |
| 6,010,445 | A | 1/2000 | Armini et al. | 6,303,901 | B1 | 10/2001 | Perry et al. |
| 6,010,530 | A | 1/2000 | Goicoechea | 6,306,176 | B1 | 10/2001 | Whitbourne |
| 6,015,541 | A | 1/2000 | Greff et al. | 6,312,459 | B1 | 11/2001 | Huang et al. |
| 6,033,582 | A | 3/2000 | Lee et al. | 6,327,772 | B1 | 12/2001 | Zadno-Azizi et al. |
| 6,042,875 | A | 3/2000 | Ding et al. | 6,331,313 | B1 | 12/2001 | Wong et al. |
| 6,048,964 | A | 4/2000 | Lee et al. | 6,335,029 | B1 | 1/2002 | Kamath et al. |
| 6,051,576 | A | 4/2000 | Ashton et al. | 6,346,110 | B2 | 2/2002 | Wu |
| 6,051,648 | A | 4/2000 | Rhee et al. | 6,358,556 | B1 | 3/2002 | Ding et al. |
| 6,056,993 | A | 5/2000 | Leidner et al. | 6,375,826 | B1 | 4/2002 | Wang et al. |
| 6,060,451 | A | 5/2000 | DiMaio et al. | 6,379,381 | B1 | 4/2002 | Hossainy et al. |
| 6,060,518 | A | 5/2000 | Kabanov et al. | 6,387,121 | B1 | 5/2002 | Alt |
| 6,066,156 | A | 5/2000 | Yan | 6,387,124 | B1 | 5/2002 | Buscemi et al. |
| 6,071,266 | A | 6/2000 | Kelley | 6,388,043 | B1 | 5/2002 | Langer et al. |
| 6,074,659 | A | 6/2000 | Kunz et al. | 6,395,326 | B1 | 5/2002 | Castro et al. |
| 6,080,177 | A | 6/2000 | Igaki et al. | 6,409,761 | B1 | 6/2002 | Jang |
| 6,080,488 | A | 6/2000 | Hostettler et al. | 6,419,692 | B1 | 7/2002 | Yang et al. |
| 6,083,258 | A | 7/2000 | Yadav | 6,423,092 | B2 | 7/2002 | Datta et al. |
| 6,093,463 | A | 7/2000 | Thakrar | 6,451,373 | B1 | 9/2002 | Hossainy et al. |
| 6,096,070 | A | 8/2000 | Ragheb et al. | 6,461,632 | B1 | 10/2002 | Gogolewski |
| 6,096,525 | A | 8/2000 | Patnaik | 6,464,720 | B2 | 10/2002 | Boatman et al. |

| | | | | | | |
|---|---|---|---|---|---|---|
| 6,479,565 B1 | 11/2002 | Stanley | | 2002/0138133 A1 | 9/2002 | Lenz et al. |
| 6,485,512 B1 | 11/2002 | Cheng | | 2002/0155212 A1 | 10/2002 | Hossainy |
| 6,492,615 B1 | 12/2002 | Flanagan | | 2002/0161114 A1 | 10/2002 | Gunatillake et al. |
| 6,494,862 B1 | 12/2002 | Ray et al. | | 2003/0033001 A1 | 2/2003 | Igaki |
| 6,494,908 B1 | 12/2002 | Huxel et al. | | 2003/0065377 A1 | 4/2003 | Davila et al. |
| 6,495,156 B2 | 12/2002 | Wenz et al. | | 2003/0093107 A1 | 5/2003 | Parsonage et al. |
| 6,503,556 B2 | 1/2003 | Harish et al. | | 2003/0099712 A1 | 5/2003 | Jayaraman |
| 6,503,954 B1 | 1/2003 | Bhat et al. | | 2003/0100865 A1 | 5/2003 | Santini, Jr. et al. |
| 6,506,437 B1 | 1/2003 | Harish et al. | | 2003/0105518 A1 | 6/2003 | Dutta |
| 6,511,748 B1 | 1/2003 | Barrows | | 2003/0105530 A1 | 6/2003 | Pirhonen |
| 6,517,888 B1 | 2/2003 | Weber | | 2003/0171053 A1 | 9/2003 | Sanders |
| 6,527,801 B1 | 3/2003 | Dutta | | 2003/0187495 A1 | 10/2003 | Cully et al. |
| 6,527,863 B1 | 3/2003 | Pacetti et al. | | 2003/0208259 A1 | 11/2003 | Penhasi |
| 6,537,589 B1 | 3/2003 | Chae et al. | | 2003/0209835 A1 | 11/2003 | Chun et al. |
| 6,539,607 B1 | 4/2003 | Fehring et al. | | 2003/0226833 A1 | 12/2003 | Shapovalov et al. |
| 6,540,776 B2 | 4/2003 | Sanders Millare et al. | | 2003/0236565 A1 | 12/2003 | Fifer |
| 6,540,777 B2 | 4/2003 | Stenzel | | 2004/0093077 A1 | 5/2004 | White et al. |
| 6,544,223 B1 | 4/2003 | Kokish | | 2004/0098095 A1 | 5/2004 | Burnside et al. |
| 6,544,543 B1 | 4/2003 | Mandrusov et al. | | 2004/0111149 A1 | 6/2004 | Stinson |
| 6,544,582 B1 | 4/2003 | Yoe | | 2004/0127970 A1 | 7/2004 | Weber |
| 6,554,854 B1 | 4/2003 | Flanagan | | 2004/0143317 A1 | 7/2004 | Stinson et al. |
| 6,555,157 B1 | 4/2003 | Hossainy | | 2004/0167610 A1 | 8/2004 | Fleming, III |
| 6,558,733 B1 | 5/2003 | Hossainy et al. | | | | |
| 6,565,599 B1 | 5/2003 | Hong et al. | | FOREIGN PATENT DOCUMENTS | | |
| 6,565,659 B1 | 5/2003 | Pacetti et al. | | | | |
| 6,569,191 B1 | 5/2003 | Hogan | | DE | 197 31 021 | 1/1999 |
| 6,569,193 B1 | 5/2003 | Cox et al. | | DE | 198 56 983 | 12/1999 |
| 6,572,644 B1 | 6/2003 | Moein | | EP | 0 108 171 | 5/1984 |
| 6,572,672 B2 | 6/2003 | Yadav et al. | | EP | 0 144 534 | 6/1985 |
| 6,574,851 B1 | 6/2003 | Mirizzi | | EP | 0 301 856 | 2/1989 |
| 6,585,755 B2 | 7/2003 | Jackson et al. | | EP | 0 364 787 | 4/1990 |
| 6,585,765 B1 | 7/2003 | Hossainy et al. | | EP | 0 397 500 | 11/1990 |
| 6,585,926 B1 | 7/2003 | Mirzaee | | EP | 0 464 755 | 1/1992 |
| 6,592,614 B2 | 7/2003 | Lenker et al. | | EP | 0 493 788 | 7/1992 |
| 6,592,617 B2 | 7/2003 | Thompson | | EP | 0 514 406 | 11/1992 |
| 6,605,154 B1 | 8/2003 | Villareal | | EP | 0 554 082 | 8/1993 |
| 6,613,072 B2 | 9/2003 | Lau et al. | | EP | 0 578 998 | 1/1994 |
| 6,626,939 B1 | 9/2003 | Burnside et al. | | EP | 0 604 022 | 6/1994 |
| 6,635,269 B1 | 10/2003 | Jennissen | | EP | 0 621 017 | 10/1994 |
| 6,645,243 B2 | 11/2003 | Vallana et al. | | EP | 0 623 354 | 11/1994 |
| 6,656,162 B2 | 12/2003 | Santini, Jr. et al. | | EP | 0 665 023 | 8/1995 |
| 6,664,335 B2 | 12/2003 | Krishnan | | EP | 0 701 802 | 3/1996 |
| 6,666,214 B2 | 12/2003 | Canham | | EP | 0 709 068 | 5/1996 |
| 6,667,049 B2 | 12/2003 | Janas et al. | | EP | 0 716 836 | 6/1996 |
| 6,669,723 B2 | 12/2003 | Killion et al. | | EP | 0 809 999 | 12/1997 |
| 6,676,697 B1 | 1/2004 | Richter | | EP | 0 832 655 | 4/1998 |
| 6,679,980 B1 | 1/2004 | Andreacchi | | EP | 0 850 651 | 7/1998 |
| 6,689,375 B1 | 2/2004 | Wahlig et al. | | EP | 0 879 595 | 11/1998 |
| 6,695,920 B1 | 2/2004 | Pacetti et al. | | EP | 0 910 584 | 4/1999 |
| 6,706,273 B1 | 3/2004 | Roessler | | EP | 0 923 953 | 6/1999 |
| 6,709,379 B1 | 3/2004 | Brandau et al. | | EP | 0 953 320 | 11/1999 |
| 6,719,934 B2 | 4/2004 | Stinson | | EP | 0 970 711 | 1/2000 |
| 6,719,989 B1 | 4/2004 | Matsushima et al. | | EP | 0 982 041 | 3/2000 |
| 6,720,402 B2 | 4/2004 | Langer et al. | | EP | 1 273 314 | 1/2003 |
| 6,746,773 B2 | 6/2004 | Llanos et al. | | GB | 2 247 696 | 3/1992 |
| 6,752,826 B2 | 6/2004 | Holloway et al. | | JP | 2001-190687 | 7/2001 |
| 6,753,007 B2 | 6/2004 | Haggard et al. | | WO | WO 89/03232 | 4/1989 |
| 6,764,505 B1 | 7/2004 | Hossainy et al. | | WO | WO 90/01969 | 3/1990 |
| 6,805,898 B1 * | 10/2004 | Wu et al. ............... 427/2.25 | | WO | WO 90/06094 | 6/1990 |
| 6,818,063 B1 | 11/2004 | Kerrigan | | WO | WO 91/12846 | 9/1991 |
| 6,846,323 B2 | 1/2005 | Yip et al. | | WO | WO 91/17744 | 11/1991 |
| 2001/0018469 A1 | 8/2001 | Chen et al. | | WO | WO 91/17789 | 11/1991 |
| 2001/0037145 A1 | 11/2001 | Guruwaiya et al. | | WO | WO 92/10218 | 6/1992 |
| 2001/0044652 A1 | 11/2001 | Moore | | WO | WO 93/06792 | 4/1993 |
| 2002/0002399 A1 | 1/2002 | Huxel et al. | | WO | WO 94/21196 | 9/1994 |
| 2002/0004060 A1 | 1/2002 | Heublein et al. | | WO | WO 95/10989 | 4/1995 |
| 2002/0004101 A1 | 1/2002 | Ding et al. | | WO | WO 95/29647 | 11/1995 |
| 2002/0062148 A1 | 5/2002 | Hart | | WO | WO 96/40174 | 12/1996 |
| 2002/0065553 A1 | 5/2002 | Weber | | WO | WO 97/10011 | 3/1997 |
| 2002/0077693 A1 | 6/2002 | Barclay et al. | | WO | WO 98/04415 | 2/1998 |
| 2002/0091433 A1 | 7/2002 | Ding et al. | | WO | WO 99/03515 | 1/1999 |
| 2002/0111590 A1 | 8/2002 | Davila et al. | | WO | WO 99/16386 | 4/1999 |
| 2002/0116050 A1 | 8/2002 | Kocur | | WO | WO 99/42147 | 8/1999 |

| | | |
|---|---|---|
| WO | WO 00/12147 | 3/2000 |
| WO | WO 00/18446 | 4/2000 |
| WO | WO 00/32238 | 6/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 2004/023985 | 3/2004 |

OTHER PUBLICATIONS

Anonymous, *Bioabsorbable stent mounted on a catheter having optical coherence tomography capabilities*, Research Disclosure, Sep. 2004, pp. 1159-1162.

Anonymous, *A Simple Approach for Glass Transition Temperature Prediction*, http://www.geocities.com/ResearchTriangle/Thinktank/4146/6400glass-temperature.html, printed May 5, 2005 (2 pages).

Anonymous, *Amorphous Polymers and the Glass Transition Temperature*, http://www.irc.leeds.ac.uk/iaps/mod1/node6.html, printed May 9, 2005 (3 pages).

Anonymous, *Appendix I—Glass Transition Temperature ($T_g$)* printed May 9, 2005 (1 page).

Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).

Anonymous, *Differential Scanning Calorimetry*, http://www.pscr.usm.edu/macrog/dsc.htm, printed May 9, 2005 (8 pages).

Anonymous, *Glass transition temperature*, http://palimpsest.stanford.edu/don/dt/dt1549.html, printed May 5, 2005 (1 page).

Anonymous, *Glass Transition Temperature*, http://islnotes.cps.msu.edu/trp/back/mol_glas.html, printed Mar. 21, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *How Big are Polymers?* printed May 9, 2005 (13 pages).

Anonymous, *Measuring and Understanding Tg (Glass Transition Temperature)*, Arlon, Application Notes (4 pages), not available.

Anonymous, *Rolling Therapeutic Agent Loading Device for Therapeutic Agent Delivery or Coated Stent* (Abstract 434009), Res. Disclos. pp. 974-975 (Jun. 2000).

Ansari, *Tubal Reanastomosis Using Absorbable Stent*, International Journal of Fertility, vol. 23, No. 4, pp. 242-243 (1978).

Ansari, *End-to-end tubal anastomosis using an absorbable stent*, Fertility and Sterility, vol. 32(2), pp. 197-201 (Aug. 1979).

Aoyagi et al., *Preparation of cross-linked aliphatic polyester and application to thermo-responsive material*, Journal of Controlled Release 32:87-96 (1994).

Baird et al., *Dielectric behaviour and morphology of polyvinylidene fluoride*, Journal of Material Science 10:1248-1251 (1975).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Black et al., *Glass Transitions of Some Block Copolymers*, Journal of Applied Polymer Science 18:2307-2310 (1974).

Bliznyuk et al., *Surface Glass Transition Temperature of Amorphous Polystyrene Measured By SFM*, pp. 1-5, not available.

Buchholz et al., *Cooling rate dependence of the glass transition temperature of polymer melts: Molecular dynamics study*, Journal of Chemical Physics 117(15):7364-7372 (Oct. 15, 2002).

Bull, *Parylene Coating for Medical Applications*, Medical Product Manufacturing News 1 pg. (Mar. 1993).

Casper et al., *Fiber-Reinforced Absorbable Composite for Orthopedic Surgery*, Polymeric Materials Science and Engineering, 53: pp. 497-501 (1985).

Chung et al., *Inner core segment design for drug delivery control of thermo-responsive polymeric micelles*, Journal of Controlled Release 65:93-103 (2000).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Devanathan et al., *Polymeric Conformal Coatings for Implantable Electronic Devices*, IEEE Transactions on Biomedical Engineering, vol. BME-27(11), pp. 671-675 (1980).

Dichek et al., *Seeding of Intravascular Stents with Genetically Engineered Endothelial Cells*, Circ. 80(5):1347-1353 (Nov. 1989).

Ding et al., *Novel Synthesis of Poly(p-phenylene sulfide) from Cyclic Disulfide Oligomers*, Macromolecules 29:4811-4812 (1996).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Elbert et al., *Conjugate Addition Reactions Combined with Free-Radical Cross-Linking for the Design of Materials for Tissue Engineering*, Biomacromolecules 2, pp. 430-441 (2001).

Fernandez-Martin et al., *Glass Transition Temperature and Heat Capacity of Heterotacticlike PMMA*, Journal of Polymer Science: Polymer Physics Edition 19:1353-1363 (1981).

Feng-Chun et al., *Assessment of Tissue Blood Flow Following Small Artery Welding with an Intraluminal Dissolvable Stent*, Microsurgery, vol. 19(3), pp. 148-152 (1999).

Forrest et al., *Effect of Free Surfaces on the Glass Transition Temperature of Thin Polymer Films*, Physical Review Letters 77(10):2002-2005 (Sep. 2, 1996).

Fryer et al., *Dependence of the Glass Transition Temperature of Polymer Films on Interfacial Energy and Thickness*, Macromolecules 34(16):5627-5634 (2001).

Fujii et al., *Investigation of the Stereoregularity of Poly(vinyl Alchohol)*, Journal of Polymer Science: Part A 2:2327-2347 (1964).

Gee et al., *The effect of ionizing radiation on the thermal properties of linear high polymers: Part 2. Nylon-6*, pp. 192-197 (1970).

Grohens et al., *Tacticity and surface chemistry effects on the glass transition temperature of thin supported PMMA films*, Mat. Res. Soc. Symp. 629:FF1.7.1-FF1.7.7 (2000).

Hahn et al., *Glow Discharge Polymers as Coatings for Implanted Devices*, ISA, pp. 109-111 (1981).

Hahn et al., *Biocompatibility of Glow-Discharge-Polymerized Films and Vacuum-Deposited Parylene*, J Applied Polymer Sci, 38, pp. 55-64 (1984).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Kelley et al., *Totally Resorbable High-Strength Composite Material*, Advances in Biomedical Polymers, 35, pp. 75-85 (1987).

Kubies et al., *Microdomain Structure In polylactide-block-poly(ethylene oxide) copolymer films*, Biomaterials 21, pp. 529-536 (2000).

Kutryk et al., *Coronary Stenting: Current Perspectives*, a companion to the Handbook of Coronary Stents 16 pgs. (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Löfgren et al., *Synthesis and Characterization of Biodegradable Homopolymers and Block Copolymers Based on 1,5-Dioxepan-2-one*, Macromolecules 27:5556-5562 (1994).

Lotz, *Phase Transitions and Structure of Crystalline Polymers*, pp. 1-27, not available.

Marconi et al., *Covalent bonding of heparin to a vinyl copolymer for biomedical applications*, Biomaterials 18(12):885-890 (1997).

Martin et al., *Enhancing the biological activity of immobilized osteopontin using a type-1 collagen affinity coating*, J. Biomed. Mater Res 70A, pp. 10-19 (2004).

Matsumaru et al., *Embolic Materials For Endovascular Treatment of Cerebral Lesions*, J. Biomater. Sci. Polymer Edn 8(7):555-569 (1997).

Mauduit et al., *Hydrolytic degradation of films prepared from blends of high and low molecular weight poly(DL-lactic acid)s*, J. Biomed. Mater. Res. v. 30, pp. 201-207 (1996).

Micoulaut et al., *Glass Transition temperature variation, crosslinking and structure in network glasses: A stochastic approach*, Europhysics Letters 47(5):568-574 (Sep. 1, 1999).

Middleton et al., *Synthetic biodegradable polymers as orthopedic devices*, Biomaterials, vol. 21, pp. 2335-2346 (2000).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Muller et al., *Advances in Coronary Angioplasty: Endovascular Stents*, Coron. Arter. Dis., 1(4), pp. 438-448 (Jul./Aug. 1990).

Nichols et al., *Electrical Insulation of Implantable Devices by Composite Polymer Coatings*, ISA Transactions, 26(4), pp. 15-18 (1987).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, Vol. XXXIX(2):129-140 (Sep./Oct. 1996).

Parravicini et al., *Crystallization of Poly(Ethylene Terephthalate) (PET) from the Oriented Mesomorphic Form*, pp. 875-885 (1994).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Peuster et al., *A novel approach to temporary stenting: degradable cardiovascular stents produced from corrodible metal-results 6-18 months after implantation into New Zealand white rabbits*, Heart 86, pp. 563-569 (2001).

Pietrzak et al., *Bioresorbable implants—practical considerations*, Bone v. 19, No. 1, Supplement Jul. 1996: 109S-119S.

Pietrzak et al., *Bioabsorbable Fixation Devices: Status for the Craniomaxillofacial Surgeon*, J. Craniofaxial Surg. 2, pp. 92-96 (1997).

von Recum et al., *Degradation of polydispersed poly(L-lactic acid) to modulate lactic acid release*, Biomaterials 16, pp. 441-445 (1995).

Redman, *Clinical Experience with Vasovasostomy Utilizing Absorbable Intravasal Stent*, Urology, vol. 20(1), pp. 59-61 (Jul. 1982).

Rogers et al., *Glass Formation in Polymers. I. The Glass Transitions of the Poly-(n-Alkyl Methacrylates)*, 61:985-990 (Jul. 1957).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, 79(2), pp. 445-457 (Feb. 1989).

Scott et al., *Ehtylene-Vinyl Acetate Semi-Batch Emulsion Copolymerization: Use of Factorial Experiments for Process Optimization*, pp. 539-555 (1993).

Shigeno, *Prevention of Cerebrovascular Spasm By Bosentan, Novel Endothelin Receptor*, Chemical Abstract 125:212307 (1996).

Sichina, *Characterization of Polymers by TMA*, Perkin Elmer Polymers technical note (9 pages), not available.

Schmidt et al., *Long-Term Implants of Parylene-C Coated Microelectrodes*, Med & Biol Eng & Comp, 26(1), pp. 96-101 (Jan. 1988).

Spagnuolo et al., *Gas 1 is induced by VE-cadherin and vascular endothelial growth factor and inhibits endothelial cell apoptosis*, Blood 103, pp. 3005-3012 (2004).

Sun et al., *Novel Copolyesters Containing Naphthalene Structure. I. From Bis(hydroxyalkyl)naphthalate and Bis[4-(2-hydroxyethoxy)aryl] Compounds*, Journal of Polymer Science: Part A: Polymer Chemistry 34:1783-1792 (1996).

Tamai et al., *Initial and 6-Month Results of Biodegradable Poly-l-Lactic Acid Coronary Stents in Humans*, Circulation, pp. 399-404 (2000).

Taylor et al., *Applied approach to film formation; The glass transition temperature evolution of plasticized latex films* (22 pages), not available.

Tsige et al., *Simulation study of the glass transition temperature in poly(methyl methacrylate)*, Physical Review E 65:021805-1-021805-8 (2002).

Tsui et al., *Biodegradable Polymeric Stents*, Current Interventional Cardiology Reports 3, pp. 10-17 (2001).

van Beusekom et al., *Coronary stent coatings*, Coronary Artery Disease 5(7):590-596 (Jul. 1994).

Völkel et al., *Targeting of immunoliposomes to endothelial cells using a single -chain Fv fragment directed against human endoglin (CD105)*, Biochemica et Biophysica Acta 1663, pp. 158-166 (2004).

Wilensky et al., *Methods and Devices for Local Drug Delivery in Coronary and Peripheral Arteries*, Trends Cardiovasc. Med. 3(5):163-170 (1993).

Yau et al. Modern Size-Exclusion Liquid Chromatography, Wiley-Interscience Publication, (1979).

Yokoyama et al., *Characterization of physical entrapment and chemical conjugation of adriamysin in polymeric micelles and their design for in vivo delivery to a solid tumor*, Journal of Controlled Release 50:79-92 (1998).

\* cited by examiner

METHOD OF POLISHING IMPLANTABLE MEDICAL DEVICES TO LOWER THROMBOGENECITY AND INCREASE MECHANICAL STABILITY

CROSS-REFERENCE

This is a continuation-in-part of application Ser. No. 10/603,889 filed on Jun. 25, 2003.

BACKGROUND OF THE INVENTION

1. Field of the Invention

This invention is directed to methods for polishing implantable medical devices, such as stents, for lower thrombogenecity and improved mechanical performance.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of a passageway. Typically, stents are capable of being compressed or crimped, so that they can be inserted or delivered through small vessels via catheters, and then expanded or deployed to a larger diameter once they are at the desired location. In addition, biological therapy can be achieved by medicating the stents. Medicated stents provide for the local administration of a therapeutic substance at the diseased site. One proposed method for medicating stents involves the use of a polymeric carrier coated onto the surface of a stent. A blend which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Stents have been made of many materials including metals and polymeric materials such as plastic, including biodegradable plastic materials. Stents have been formed from wire, tube stock, etc. Stents have also been made from sheets of material which are rolled into a cylindrical shape. A medicated stent may be fabricated by coating the surface of either a metal or polymeric scaffolding or substrate with a polymeric carrier. A drug can also be incorporated into a polymer from which a stent is made. In addition, the structure of a stent is typically composed of a pattern that allows the stent to be radially expandable. The pattern should be designed to maintain the necessary longitudinal flexibility and radial rigidity of the stent. Longitudinal flexibility facilitates delivery of the stent and radial rigidity is needed to hold open a bodily lumen.

The biocompatibility of an implantable medical device, such as a stent, is extremely important for successful treatment of a bodily lumen. One measure of biocompatibility is the tendency for an implantable medical device to form thrombus. The surface finish of an implantable medical device is an important factor in thrombus formation. Certain surface features such as cracks, pits, or jagged edges substantially increase formation of thrombus. Such imperfections tend to be a by-product of a fabrication process. In addition, imperfections in the surface of an implantable medical device may cause mechanical instability. Surface cracks or other imperfections tend to serve as sites at which stress applied to an implantable medical device is concentrated. Therefore, imperfections can result in the enlargement of existing cracks or formation of new cracks. This can occur when stress is applied to the implantable medical device, for example, during crimping or deployment.

SUMMARY

The present invention is directed to embodiments of a method of polishing an implantable medical device. In one embodiment, the method may include positioning an implantable medical device on a support. At least a portion of a surface of the implantable medical device may include a polymer. The method may further include contacting a fluid with at least a portion of the surface of the positioned implantable medical device. The fluid may be capable of dissolving at least a portion of the polymer at or near the surface of the implantable medical device. In some embodiments, the fluid may be allowed to modify at least a portion of the surface of the positioned medical device. In certain embodiments, the method may further include removing all or a majority of the contacted fluid from the surface of the implantable medical device. The modified portion of the surface, after removal of the contacted fluid, may be less thrombogenetic and more mechanically stable than an unmodified surface.

DETAILED DESCRIPTION OF THE INVENTION

For the purposes of the present invention, the following terms and definitions apply:

"Thrombosis" refers to the formation or presence of a blood clot or "thrombus" within a blood vessel. The blood clot results from aggregation of blood components, primarily fibrin and platelets. The thrombus frequently results in vascular obstruction.

"Lysis" refers to a process of disintegration or dissolution, for example, of cells.

"Pseudopodia" refers to a temporary protrusion or retractile process of the cytoplasm of a cell that functions in a locomotive or food gathering capacity.

Figure 1:
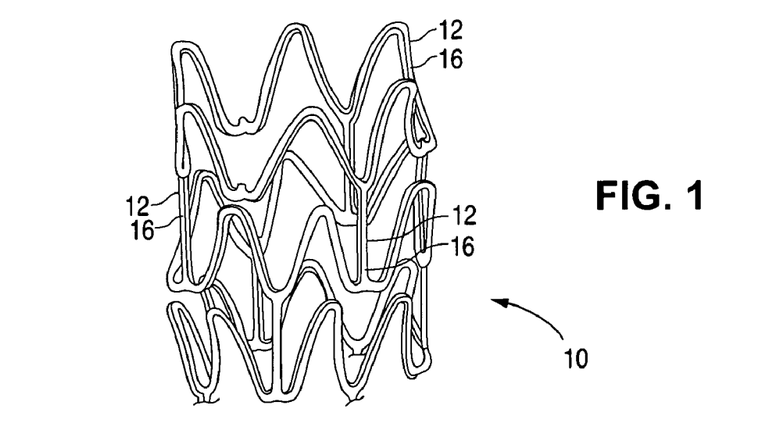
FIG. 1 depicts a stent.
Figure 2:
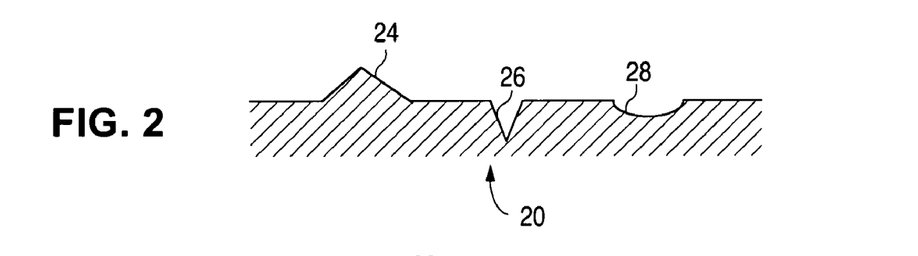
FIGS. 2 and 3 depict diagrams of a surface of a stent.

When referring to a polymeric surface of an implantable medical device, unless otherwise specified, this includes a device made from a polymer or coated with a polymer. The underlying substrate that is coated can be polymeric, metallic, ceramic, or made from any suitable material. The polymer surface of an implantable medical device often includes various types of imperfections or features that tend to make the device more susceptible to thrombosis and/or mechanical instability. Such imperfections or features tend to activate fibrin and/or platelets to form thrombus. These imperfections are often formed during the fabrication of the implantable medical device. For example, the imperfections may be a by-product of an injection molding process or a coating process. The imperfections may include cracks, pitting, and/or jagged edges. FIG. 1 depicts a stent 10 that includes struts 12 with a surface 16. FIG. 2 depicts a surface 20 which is an expanded cross-section of a portion of surface 16 of stent 10. Surface 20 includes a jagged edge 24, a crack 26, and a pit 28.

Figure 3:
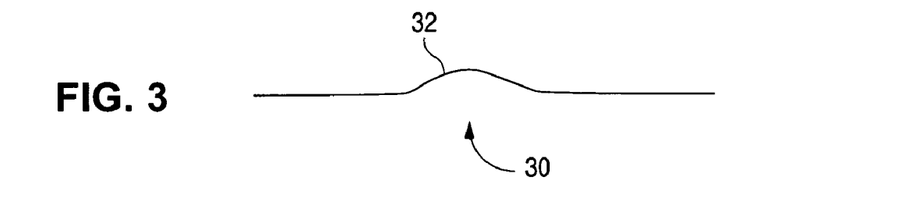

The presence of such imperfections on the surface of an implantable medical device tends to facilitate the rapid formation of thrombus when implanted in a bodily lumen. It is believed that thrombus formation is facilitated by such imperfections. Without being bound by any particular theory, imperfections on a surface may serve as sites at which platelets may attach which may then lead to thrombus formation. Removing and/or reducing such imperfections may decrease the number of sites for attachment to a surface and/or reduce the tendency for platelets to attach to a surface, respectively, of an implantable medical device. Therefore, thrombus formation may be significantly reduced. Reducing an imperfection may refer to reducing the degree or size of an imperfection in a way that improves surface quality. For example, reducing an imperfection may correspond to smoothing a jagged edge. FIG. 3 depicts a surface 30 which is another expanded cross-section of surface 16 of stent 10 depicted in FIG. 1. Feature 32 may result in significantly less platelet attachment than jagged edge 24 in FIG. 2. As a result, surface 30 may result in significantly less thrombosis than surface 20 proximate to jagged edge 24. Therefore, it may be advantageous to modify the surface of an implantable medical device to reduce or remove imperfections from the surface to reduce thrombus formation.

Furthermore, the presence of features such as cracks or pitting in an implantable medical device may cause mechanical instability in the implantable medical device. In general, some features, in particular cracks, tend to result in stress concentration localized at or near the imperfection. Such features may be referred to as "stress concentrators." Irregularities or discontinuities in the shape of an object, such as crack 26 in FIG. 2, result in steep gradients of stress at or near the irregularity or discontinuity. Stress is concentrated at an irregularity or discontinuity because a load on an object cannot be uniformly distributed across the full area of the object. Therefore, the load must be redistributed across a missing cross-section of the object. Moreover, stress concentrators may lead to failure of a material since fracture always starts at some point of stress concentration. Failure and fracture mechanics of polymers and other types of materials are well known and are discussed in many publications, for example, "Deformation and Fracture Mechanics of Engineering Materials," Richard W. Hertzberg, 4th edition, John Wiley & Sons, December 1995.

Implantable medical devices are subjected to stress both before and during treatment. For example, implantable medical devices are placed under stress during crimping and deployment. Therefore, it may be desirable to modify the surface of an implantable medical device to reduce or remove imperfections from its surface to increase mechanical stability of the implantable medical device.

The method described herein may be particularly useful for implantable medical devices in which at least a portion of the surface of the implantable medical device is polymeric. The device can be made partially or completely from a biodegradable, bioabsorbable, or biostable polymer. The polymer may be purified. A polymer-fabricated device may serve as a substrate for a polymer-based coating. The polymer-based coating may contain, for example, an active agent or drug for local administration at a diseased site. Alternatively, an implantable medical device may include a non-polymer substrate with a polymer-based coating. Examples of implantable medical devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure or substrate of the device can be of virtually any design. A non-polymer substrate of the device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like. For coating applications, it is understood that after the process of degradation, erosion, absorption, and/or resorption has been completed, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

An implantable medical device, such as a stent can be completely or at least in part be made from a biodegradable polymer or combination of biodegradable polymers, a biostable polymer or combination of biostable polymers, or a combination of biodegradable and biostable polymers. In some embodiments, a surface of an implantable medical device such as a stent can be coated with a biodegradable polymer or combination of biodegradable polymers, a biostable polymer or combination of biostable polymers, or a combination of biodegradable and biostable polymers.

Representative examples of polymers that may be used in fabricating an implantable medical device using the methods disclosed herein include poly(N-acetylglucosamine) (Chitin), Chitoson, poly(hydroxyvalerate), poly(lactide-co-glycolide), poly(hydroxybutyrate), poly(hydroxybutyrate-co-valerate), polyorthoester, polyanhydride, poly(glycolic acid), poly(D,L-lactic acid), poly(glycolic acid-co-trimethylene carbonate), poly(trimethylene carbonate), co-poly (ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as polyester amides, Nylon 66, and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in manufacturing an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), poly(L-lactic acid), poly(caprolactone), ethylene-vinyl acetate copolymers, and polyethylene glycol.

Some embodiments of a method of polishing a stent surface may use a fluid that is a solvent for the polymeric surface of the stent. "Solvent" is defined as a substance capable of dissolving or dispersing one or more other substances or capable of at least partially dissolving or dispersing the substance(s) to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure. A second fluid can act as a non-solvent for the impurity. "Non-solvent" is defined as a substance incapable of dissolving the other substance. The non-solvent should be capable of dissolving only less than 0.1 mg of the polymer in 1 ml of the non-solvent at ambient temperature and ambient pressure, and more narrowly only less than 0.05 mg in 1 ml at ambient temperature and ambient pressure.

An embodiment of a method of polishing an implantable medical device may include positioning an implantable medical device on a support. At least a portion of the surface of the implantable medical device may be composed of a polymer. The method may further include contacting a fluid with at least a portion of the surface of the positioned implantable medical device. The fluid may be capable of dissolving at least a portion of the polymer at or near the surface of the implantable medical device. In certain embodiments, the fluid may be allowed to modify at least a portion of the surface of the positioned implantable medical device. In one embodiment, the fluid is free (100%) from any polymeric materials, active agents, or drugs. The fluid can be a pure solvent or a combination of one or more pure solvents. The method may then include removing all or a majority of the contacted fluid from the surface of the implantable medical device. After removal of the contacted fluid, the modified portion of the surface may be less thrombogenetic and more mechanically stable than an unmodified surface.

Additionally, some embodiments of the method may further include removing at least some impurities at or near the surface of the implantable medical device prior to contacting the surface of the implantable medical device with the fluid. Impurities may include particles and/or contaminants that may reduce the effectiveness of the polishing process. One method of removing impurities may include ultrasonic cleaning. In an ultrasonic cleaning process the implantable medical device may be immersed in a bath of a suitable fluid. Representative examples of suitable fluids may include alcohols such as isopropyl alcohol, water, or any other fluid that is inert to the polymer during the time frame of the cleaning process. Removal of impurities may be achieved by subjecting the bath to ultrasonic cavitation. Cavitation refers to the formation of partial vacuums in a liquid. Standard ultrasonic baths operate at a frequency of about 40 kHz. The implantable medical device may be subjected to the ultrasonic bath for about one minute to about ten minutes, or more narrowly from about one to about three minutes. Ultrasonic cleaning may be followed by rinsing and drying of the implantable medical device. Rinsing may be performed with the cleaning solution. The device may be air dried, or baked in an oven.

It is desirable to maximize the surface area of the implantable medical that is polished. Therefore the support for the implantable medical device may be selected such that contact between the support and the device is minimized. In one embodiment, the implantable medical device may be positioned on a mandrel. A mandrel refers to a substantially cylindrical shaft that may serve as an axis. Typically, a madrel is configured to rotate about its cylindrical axis. A substantially cylindrical implantable medical device such as that depicted in FIG. 1 may be positioned about the axis of the mandrel. A tubular mandrel that is inserted into the bore of a stent can, however, mask the inner surface of the stent so as to prevent proper polishing of the inner surface of the stent. Accordingly, it is preferable to use a support assembly that allows for proper access to the inner or luminal surface of the stent and not just the outer or abluminal surface of the stent. The mandrel can include, for example, a first element that supports a first end of the stent and a second element that supports a second end of the stent. Examples in the patent literature teaching these types of mandrels include U.S. Pat. No. 6,527,863 to Pacetti et al. and U.S. Pat. No. 6,605,154 to Villareal. The madrel, accordingly does not make contact with a luminal surface of the stent and allows for proper modification of all surfaces.

Figure 4:
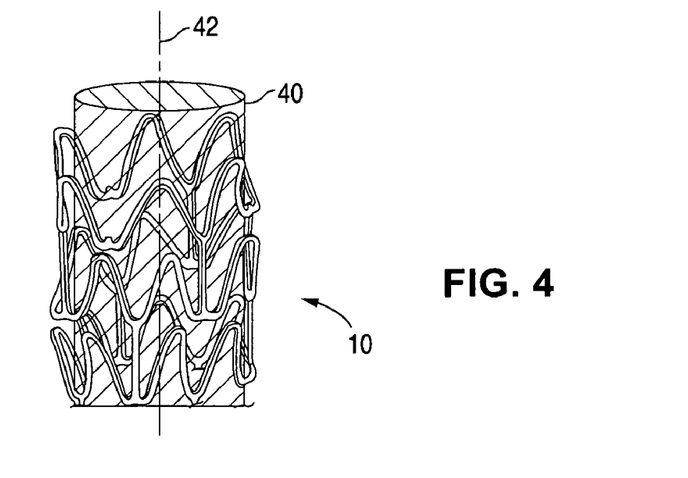
FIG. 4 depicts a stent positioned on a mandrel.

Furthermore, contacting a fluid with at least a portion of a surface of the positioned implantable medical device may be performed in several ways. In one embodiment, contacting a fluid with at least a portion of the surface may include translating the positioned implantable medical device through a stream of the fluid. In one embodiment, the stream may be an atomized stream of small droplets. In addition, in some embodiments, the implantable medical device may be rotated during the contacting of the fluid. For example, the medical device may be positioned on a rotating mandrel. Rotation may facilitate a more uniform and complete coverage of the fluid on the surface of the implantable medical device. FIG. 4 depicts implantable medical device 10 from FIG. 1 positioned on mandrel 40. The mandrel may be rotated about axis 42 during the contacting of the fluid with the surface of the implantable medical device.

In some embodiments, the stream of fluid can also be applied by spraying the fluid onto the stent with a conventional spray apparatus, or applied by other metering devices. For instance, the stent can be sprayed for one to ten spray cycles (i.e., back and forth passes along the length of the stent) using a spray apparatus to deposit about 1 ml to about 500 ml, more narrowly 5 ml to about 20 ml, of the fluid onto the stent. The spray process can take place in a vacuum chamber at a reduced pressure (e.g., less than 300 mm Hg) in order to raise the fluid concentration in the vapor phase.

Alternatively, a fluid may be contacted with the surface of the implantable medical device by hand caulking with an applicator. The applicator may include a handle with material at one end soaked with the fluid. For example, the material may be a brush, sponge, or cloth. In addition, a fluid may be vapor deposited on the surface of the implantable medical device. Additionally, an implantable medical device may be contacted with fluid by immersing the device in a bath of the fluid.

In certain embodiments, allowing the fluid to modify at least a portion of the surface of the implantable medical device may include allowing the fluid to reduce and/or remove all or a substantial portion of undesirable features from the surface that facilitate thrombosis on or mechanical instability of the implantable medical device. Since the fluid is capable of dissolving the polymer, the fluid may dissolve at least a portion of the surface of the implantable medical device to form a polymer solution. Representative examples of fluids that may be used to polish an implantable medical device include chloroform, acetone, chlorobenzene, ethyl acetate, 1,4-dioxane, ethylene dichloride, 2-ethyhexanol, and combinations thereof. The polymer solution may tend to flow at or near the surface. The formation and flow of the polymer solution may act to substantially reduce and/or remove features that facilitate thrombosis on or mechanical instability of the implantable medical device. In an embodiment, the fluid may be allowed to modify the surface of the positioned implantable medical device for a selected period of time prior to removal from the surface.

In some embodiments, the fluid may be selected to achieve a desired degree of modification during a selected period of time. Equivalently, the fluid may be selected to dissolve polymer to a desired degree during a selected period of time. Generally, the greater the solubility of the polymer in a fluid, the greater the amount of polymer dissolved at or near the surface of the implantable medical device. A parameter that is useful in characterizing the tendency of a fluid to dissolve a polymer is the solubility parameter, δ. A widely accepted unit of the solubility parameter is the Hildebrand, which is equal to 1 $(cal/cm^3)^{1/2}$. Solubility parameters of selected fluids are shown in Table 1.

TABLE 1

Solubility parameters of fluids at 25° C.

| Fluid | Solubility Parameter $(cal/cm^3)^{1/2}$ |
|---|---|
| Chloroform | 9.3 |
| Acetone | 10.0 |
| Chlorobenzene | 9.5 |
| Ethyl acetate | 9.1 |
| Ethylene dichloride | 9.8 |
| 2-ethyhexanol | 9.5 |
| 1,4-dioxane | 9.9 |

It is expected that the greatest tendency of a polymer to dissolve occurs when its solubility parameter substantially matches that of the solvent. A fluid with a tendency to dissolve a polymer that is too high may cause an undesirable degree of modification of the surface before the fluid can be removed. Alternatively, a fluid with a tendency to dissolve polymer that is too low, may require too long of a time to achieve a desired degree of modification, reducing manufacturing efficiency. In addition, a fluid may be selected based on other parameters such as viscosity and the ability of the fluid to flow across the surface of the surface of the polymer.

In some embodiments, the tendency of a fluid to dissolve a polymer may be optimized. For instance, the fluid may be a mixture of two or more fluids. The polymer may be insoluble or substantially insoluble in at least one of the fluids. For instance, at least one of fluids may be a non-solvent for the polymer. For example, chloroform has a tendency to dissolve poly(D,L-lactic acid), while poly(D,L-lactic acid) is substantially insoluble in methanol. Since chloroform and methanol are mutually soluble, a fluid with a desired tendency to dissolve the polymer may be attained by adjusting the ratio of the components in a mixture.

Additionally, if a polymer stent surface contains a drug, it may be desirable to select a solvent that is a non-solvent for the drug. The use of a fluid that is a mutual solvent for both the polymer and the drug may be undesirable because the solvent may act as a stimulus to the drug in the polymer. A stimulus increases the permeability of the drug in the polymer surface. As a result, a nonuniform composition of the drug may be created with a concentration of drug greater near the polished surface. In addition, the total drug content may be decreased through dissolution of the drug in the solvent. A nonuniform composition of the drug and a decrease in the drug content may both adversely affect the treatment of a diseased site in a bodily lumen.

In an embodiment, a majority of the contacted fluid may be removed from the surface of the implantable medical device a selected period of time after contacting the fluid with at least a portion of the surface. As discussed above, failure to remove the fluid may result in an undesirable degree of modification of the surface of the implantable medical device. Some embodiments may include removing a majority of the contacted fluid from the surface of the implantable medical device by contacting or blowing the implantable medical device with a stream of an inert gas such as nitrogen, argon, etc. The inert gas may be contacted or blown on the device for between about 30 seconds to about three minutes. The stent, mounted on a support, may be positioned between about 1 mm and about 200 mm, or more narrowly between about 10 mm and about 50 mm from a nozzle of an ejecting stream of inert gas. The support may be rotated to facilitate uniform removal of the fluid from the stent. The flow rate of the gas may be optimized to obtain quick and efficient removal of the fluid without disturbing the surface structure of the stent. The inert gas may be at ambient temperature. Alternatively, the temperature of the inert gas stream may be at a temperature greater than ambient temperature and less than or equal to the melting temperature of the polymer. The "melting temperature", $T_m$, of a polymer is the highest temperature at which a crystal lattice in the polymer is stable. If the polymer includes an active agent, it is desirable for the temperature of the polymer to be below a range at which the active agent may be degraded. A temperature range in which active agents may degrade may be at temperatures above about 100° C., or more narrowly, above about 80° C.

In some embodiments, the implantable medical device may be subjected to additional processing to remove a substantial portion of any remaining fluid. In an embodiment, at least some fluid may be removed by applying heat to the implantable medical device. For example, the implantable medical device may be heated between about fifteen minutes and about 120 minutes in an oven. The heating may be performed in a vacuum. The application of heat can be performed after blowing of the inert gas. Heat may be applied within a range of temperature greater than ambient temperature and less than the melting temperature of the polymer. As mentioned above, if the polymer includes an active agent, it is desirable for the temperature to be below a range at which the active agent may be degraded.

EXAMPLE

Some embodiments of the present invention are illustrated by the following Example. The Example is being given by way of illustration only and not by way of limitation. The Example illustrates the influence of the method of polishing an implantable medical device on blood biocompatibility. The blood compatibility of five stents was measured from two experimental runs. The parameters and data are not to be construed to unduly limit the scope of the embodiments of the invention.

Blood biocompatibility measurements were performed on a number of stents using the Chandler loop method. The Chandler loop method is well known in the art and is described in detail elsewhere. Quart. J. Exp. Physiol., 46, 1 (1961), A. B. Chandler, Lab. Investigations, 1, 110 (1958). The Chandler loop apparatus includes loops or tubes in which testing of an implantable medical device is performed. An implantable medical device may be inserted into a loop along with blood. The loops are then rotated for the duration of a test run to simulate flow in a vessel.

Blood compatibility was evaluated and/or measured in three ways. First, some of the samples were inspected visually by an optical microscope. Second, the platelet morphology and fibrin structure of the stent samples were examined using a scanning electron microscope (SEM). Finally, a quantitative measure of the thrombus formation was obtained from measurement of fluorescently labeled platelets using a fluorescent plate reader.

The influence of polishing by methods disclosed herein on thrombogenecity was evaluated for a poly(lactic acid) (PLA) polymeric stent with no coating and a PLA polymeric stent with a PLA coating. Each of these stents was obtained from Bioabsorbable Vascular Solutions in Mountainview, Calif. The unpolished and polished samples were prepared in two separate Chandler loop runs. Each Chandler loop run included a control stent. The control stent was used as a reference or control for evaluating the blood biocompatibility of the other stents in each run. The control stent in each run was a Solef-coated metallic Vision stent obtained from Guidant Corporation in Santa Clara, Calif. The Solef-coated stent is a non-bioerodable bare metal stent (BMS) that is known to have low thrombogenecity. A poly(n-butyl methacrylate) (PBMA) primer was used on the control stent. The primer is used to improve adhesion of the SOLEF to a substrate and also results in an acceptably low thrombogenecity for the surface. All of the stents were 3 mm in diameter and 8 mm in length. A summary of the stents is shown in Table 2.

TABLE 2

Summary of the stents used in Chandler Loop tests.

| Stent # | Stent | Run | Polished | Stent Material | Coating | Primer |
|---|---|---|---|---|---|---|
| 1 | In-house | 1 | No | PLA 80/20 | None | None |
| 2 | In-house | 1 | No | PLA 80/20 Blend | PLA 80/20 Blend, 115 µg | None |
| 3 | Vision (Control) | 1 | No | Cobalt Chrome | Solef, 311 µg | PBMA 44 µg |
| 4 | In-house | 2 | Yes | PLA 80/20 Blend | None | None |
| 5 | In-house | 2 | Yes | PLA 80/20 Blend | PLA 80/20 Blend, 115 µg | None |
| 6 | Vision (Control) | 2 | No | Cobalt Chrome | Solef, 311 µg | PBMA 44 µg |

The Chandler apparatus as used for this investigation can accommodate a total of 24 loops. An "arm" of the apparatus corresponds to four loops. Each loop holds one stent and has an inside diameter of 3 mm. Four samples of each stent were tested in each of the two runs. One of the four samples was used for imaging and three of the samples were used for average thrombus quantification.

Fresh porcine blood was collected on the morning of the day of the experimental runs. An anticoagulant, heparin, was added to the blood to give a concentration of 2 U/ml (units per ml) in the blood. In addition, a fluorescent dye, mepacrine HCl, was added to the whole blood as a fluorescent tag for the platelets. Previous studies have reported a concentration of 10 µMoles mepacrine did not alter platelet activity.

In each run, the stents were deployed individually in medical grade PVC tubing. 2.5 ml of the porcine blood was then added to each tube. A sleeve was used to close the loop on the outside diameter of each tube. Aside from the tubing lumen and the stent, no other foreign material was exposed to the blood. The loops were then positioned on the Chandler device and were allowed to run for 2 hours at 37° C. and 24 RPM which is equivalent to a 100 ml/min flow of blood in a 3.0 mm tube. After each run was completed, the blood was removed from each loop. Each of the stents was gently rinsed with phosphate buffered saline (PBS). One of the four stents in each arm was used for imaging and three of the four were used for thrombus quantification.

The stents for use in SEM imaging were fixed with 2.5% glutaraldehyde for an hour. The stents then underwent a serial exchange with increasing ethanol in the next three hours to preserve the three-dimensional structure of the blood cells. The stents were then air dried overnight. Before imaging, the stents were inspected visually by optical microscope. Finally, the stents were examined by a scanning electron microscope (SEM). Platelet morphology and fibrin structure were examined by SEM at high magnifications. The morphology of the platelets is important for providing insight on whether or not the platelets were being activated by the coatings. In the worst case, activated platelets change their shapes from a disc-like form to a globular form with pseudopodia extensions. The presence of fibrin mesh also indicates a severe thrombogenecity property of materials.

Figure 5:
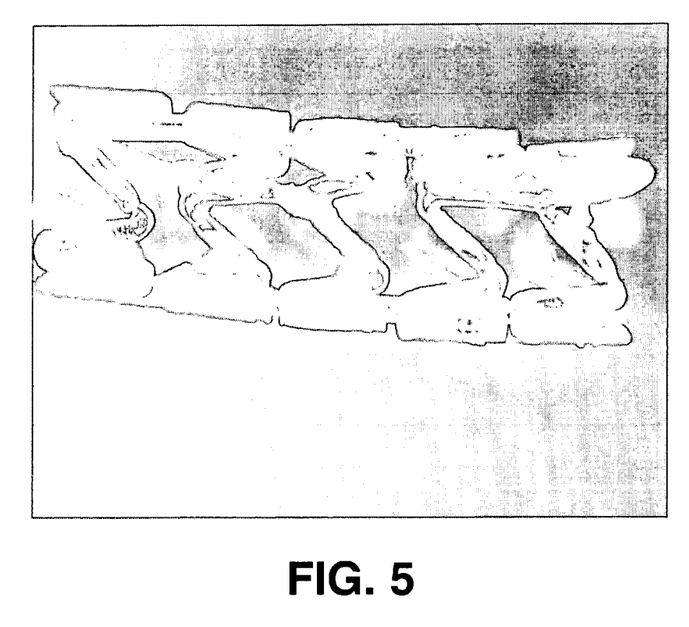
FIGS. 5 and 6 depict optical micrographs of stents.
Figure 6:
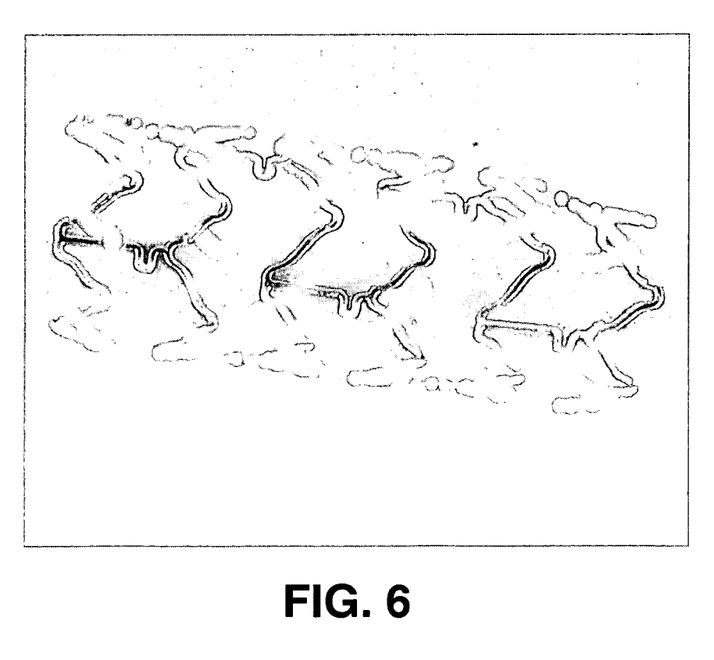

FIGS. 5 and 6 depict optical micrographs of stents #1 and #3. An examination of FIGS. 5 and 6 indicated that stent #1 resulted in more thrombus formation than the control stent, stent #3, in run 1.

Figure 7:
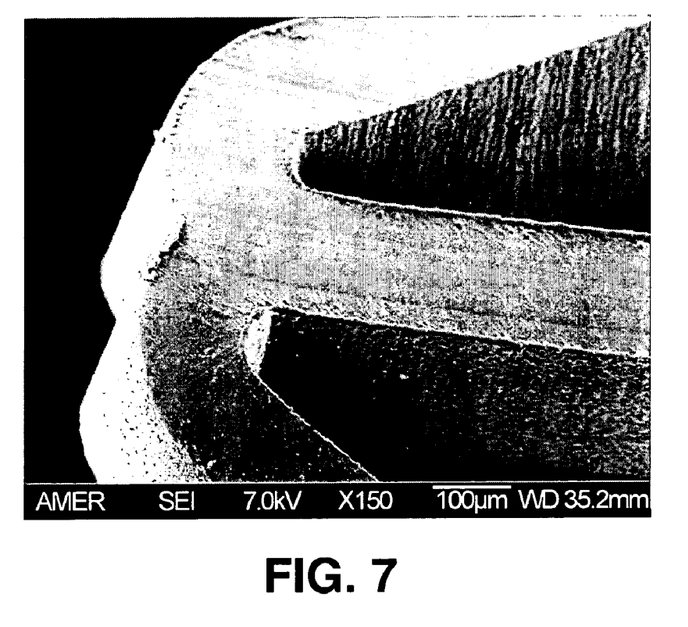
FIGS. 7 and 8 depict SEM images of the surface of a stent.
Figure 8:
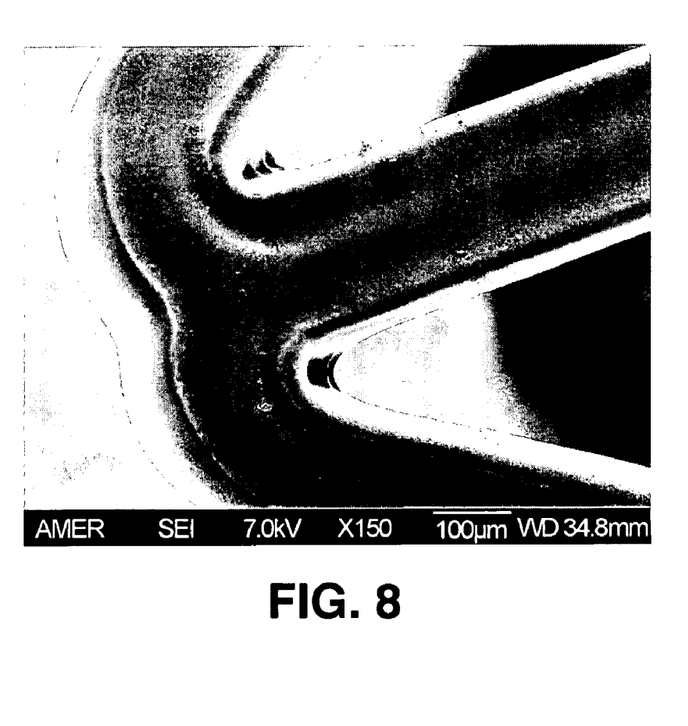

FIGS. 7 and 8 depict SEM images of representative stents before and after polishing, respectively. FIG. 7 depicts the surface of an unpolished stent and FIG. 8 depicts the surface of a polished stent. Polishing the stent has significantly reduced and/or eliminated imperfections on the surface of the stent.

Thrombus formation may be quantified by measuring the fluorescent signals from the mepacrine on blood cells that adhered to the stent surface. Blood cells that adhered to the stent surface were lysed by 1% sodium dodecyl sulphate (SDS) to release mepacrine from the platelets. The fluorescent signals from the mepacrine in the supernatant were collected and quantified by a fluorescent plate reader with an excitation wavelength at 420 nm and an excitation wavelength at 500 nm. The amount of thrombus for each stent type was normalized to the control stents in each run.

Figure 9:
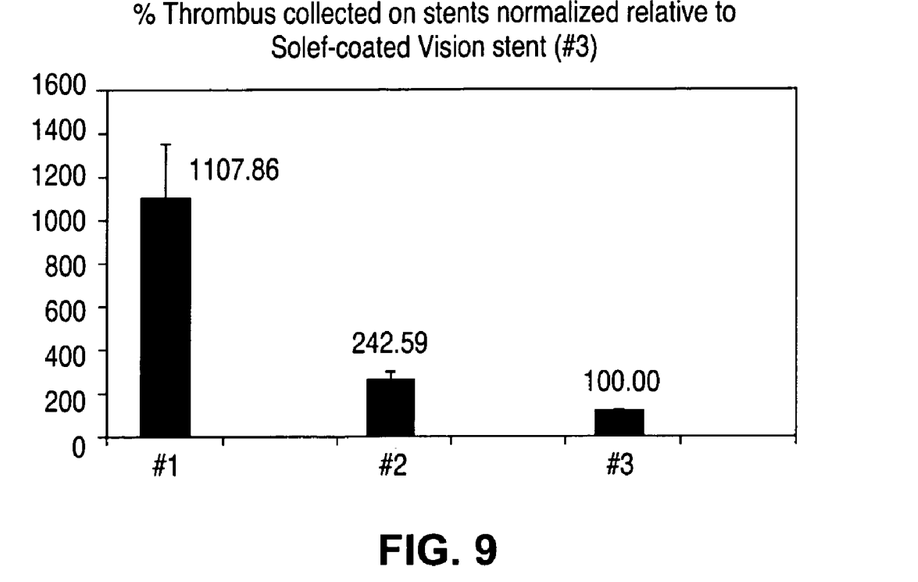
FIGS. 9 and 10 depict measured thrombosis on stents.
Figure 10:
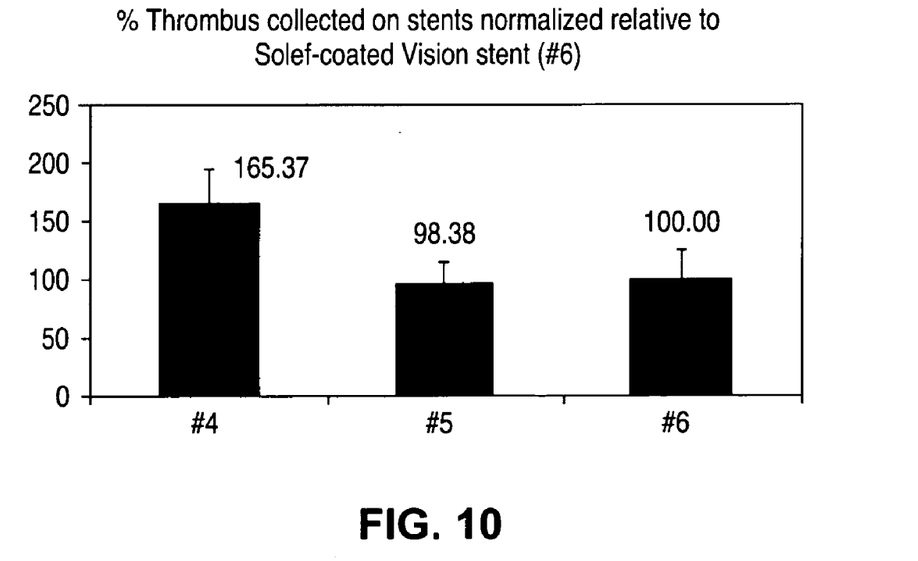

FIG. 9 shows the amount of platelets measured based on this method described above for run 1, the unpolished stents and the control. The percent error propagation is also shown. The y-axis is the percent thrombus collected on the stents normalized with respect to the control stent #3. The values for each stent are an average of the measured thrombus of three samples. FIG. 9 shows that the unpolished polymeric stent #1 has more than 11 times the thrombus of the control stent #3. FIG. 9 shows that the unpolished, coated polymeric stent #2 has about 2.4 times the thrombus of the control stent #3. FIG. 10 shows the amount of platelets measured based on this method described above for run 2, the polished stents, and the control stent. The polished, uncoated polymeric stent #4 has about 1.65 times the thrombus of the control stent #6. The polished, coated stent #5 has slightly less thrombus than the control stent #6. The results of the two runs are summarized in Table 3.

TABLE 3

Results of thrombus quantification.

| Stent # | Stent | Run | Polished | % of Control - Solef-coated BMS |
|---|---|---|---|---|
| 1 | In-house | 1 | No | 1107.86 |
| 2 | In-house | 1 | No | 242.59 |
| 3 | Vision (Control) | 1 | No | 100 |
| 4 | In-house | 2 | Yes | 165.37 |
| 5 | In-house | 2 | Yes | 98.38 |
| 6 | Vision (Control) | 2 | No | 100 |

These results demonstrate that polishing stents using the methods described herein can dramatically decrease thrombus formation on the surface of the stents. However, the results of these tests may not be extrapolated significantly beyond the two hour time frame of these tests. It is believed that a bioerodable polymer surface, such as a PLA surface, and its degradation products may impact blood compatibility in longer term tests.

What is claimed is:

1. A method of polishing an implantable medical device, comprising:

positioning an implantable medical device on a support, wherein at least a portion of a surface of the implantable medical device comprises a polymer;

contacting a fluid with at least a portion of the surface of the positioned implantable medical device, wherein the fluid is capable of dissolving at least a portion of the polymer at or near the surface of the implantable medical device;

allowing the fluid to modify at least a portion of the surface of the positioned medical device; and removing all or a majority of the contacted fluid from the surface of the implantable medical device, wherein the modified portion of the surface after removal of the contacted fluid is less thrombogenetic and more mechanically stable than an unmodified surface.

2. The method of claim 1, wherein the implantable medical device is a stent.

3. The method of claim 1, wherein the polymer comprises a bioabsorbable polymer.

4. The method of claim 1, wherein the polymer is selected from the group consisting of poly(N-acetylglucosamine), Chitoson, poly(trimethylene carbonate) and copolymers thereof, an ethylene vinyl alcohol copolymer, poly(butyl methacrylate), poly(vinylidene fluoride-co-hexafluororpropene), polyvinylidene fluoride, poly(L-lactic acid), poly(D, L-lactic acid), poly(caprolactone), an ethylene-vinyl acetate copolymer and polyethylene glycol.

5. The method of claim 1, wherein contacting the fluid with at least a portion of the surface of the positioned implantable medical device comprises translating the positioned implantable medical device through a stream of the fluid.

6. The method of claim 1, wherein the fluid is allowed to modify the surface of the positioned implantable medical device for a selected period of time sufficient to reduce thrombogeneity and increase mechanical stability of the device.

7. The method of claim 1, further comprising removing at least some impurities at or near the surface of the implantable medical device prior to contacting the surface of the implantable medical device with the fluid.

8. The method of claim 1, wherein the implantable medical device is positioned on a mandrel.

9. The method of claim 1, further comprising rotating the implantable medical device during the contacting of the fluid with at least a portion of the surface of the positioned implantable medical device.

10. The method of claim 1, wherein the fluid is selected from the group consisting of chloroform, acetone, chlorobenzene, ethyl acetate, 1,4-dioxane, ethylene dichloride, 2-ethyhexanol, and combinations thereof.

11. The method of claim 1, wherein the fluid comprises a mixture comprising at least two components, wherein the polymer is insoluble in at least one of the components.

12. The method of claim 1, wherein allowing the fluid to modify at least a portion of the surface of the implantable medical device comprises allowing the fluid to reduce and/or remove all or a substantial portion of features from the surface of the implantable medical device that facilitate thrombosis on or mechanical instability of the implantable medical device.

13. The method of claim 12, wherein the features comprise imperfections at or near the surface of the implantable medical device.

14. The method of claim 12, wherein the features comprise at least one jagged portion at or near the surface of the implantable medical device.

15. The method of claim 12, wherein the features comprise at least one pit at or near the surface of the implantable medical device.

16. The method of claim 12, wherein the features comprise at least one crack at or near the surface of the implantable medical device.

17. The method of claim 1, wherein allowing the fluid to modify at least a portion of the surface of the implantable medical device comprises allowing the fluid to dissolve at least a portion of the surface of the implantable medical device to form a polymer solution.

18. The method of claim 17, wherein allowing the fluid to modify at least a portion of the surface of the implantable medical device further comprises allowing the polymer solution to flow at or near the surface of the implantable medical device, and wherein the formation and flow of the polymer solution act to substantially or completely reduce and/or remove features that facilitate thrombosis on or mechanical instability of the implantable medical device.

19. The method of claim 1, wherein removing a majority of the contacted fluid from the surface of the implantable medical device comprises blowing an inert gas on the implantable medical device.

20. The method of claim 19, wherein removing a majority of the contacted fluid from the surface of the implantable medical device further comprises exposing the implantable medical device to heat and/or a vacuum.

21. The method of claim 1, wherein the majority of the contacted fluid is removed when a desired degree of modification is achieved.

* * * * *